(12) United States Patent
Barrett et al.

(10) Patent No.: US 8,380,272 B2
(45) Date of Patent: Feb. 19, 2013

(54) PHYSIOLOGICAL SENSOR

(75) Inventors: Bruce J. Barrett, Birmingham, MI (US); Oleg Gonopolsky, West Bloomfield, MI (US); Ronald A. Widman, Macomb, MI (US); Rick Scheuing, Rochester Hills, MI (US)

(73) Assignee: Covidien LP, Mansfield, MA (US)

( * ) Notice: Subject to any disclaimer, the term of this patent is extended or adjusted under 35 U.S.C. 154(b) by 1459 days.

(21) Appl. No.: 11/963,174

(22) Filed: Dec. 21, 2007

(65) Prior Publication Data

US 2009/0163775 A1   Jun. 25, 2009

(51) Int. Cl.
*A61B 5/1455* (2006.01)

(52) U.S. Cl. .................. 600/323; 600/310; 600/322

(58) Field of Classification Search .......... 600/310, 600/322, 323, 331, 336, 340, 344, 473, 476; 356/41; 315/185 R, 224
See application file for complete search history.

(56) References Cited

U.S. PATENT DOCUMENTS

| | | | |
|---|---|---|---|
| 4,848,901 A | 7/1989 | Hood, Jr. | |
| 4,859,057 A | 8/1989 | Taylor et al. | |
| 4,867,557 A * | 9/1989 | Takatani et al. | 600/323 |
| 4,934,372 A | 6/1990 | Corenman et al. | |
| 5,368,224 A | 11/1994 | Richardson et al. | |
| 5,783,821 A | 7/1998 | Costello, Jr. | |
| 6,044,283 A | 3/2000 | Fein et al. | |
| 6,356,774 B1 | 3/2002 | Bernstein et al. | |
| 6,697,655 B2 | 2/2004 | Sueppel et al. | |
| 6,760,610 B2 | 7/2004 | Tschupp et al. | |
| 6,882,874 B2 | 4/2005 | Huiku et al. | |
| 2001/0005773 A1 | 6/2001 | Larsen et al. | |
| 2002/0016536 A1 | 2/2002 | Benni | |
| 2002/0062071 A1 | 5/2002 | Diab et al. | |
| 2002/0082489 A1 | 6/2002 | Casciani et al. | |
| 2005/0187452 A1 | 8/2005 | Petersen et al. | |
| 2007/0149864 A1* | 6/2007 | Laakkonen | 600/323 |

FOREIGN PATENT DOCUMENTS

| | | |
|---|---|---|
| DE | 4210102 A1 | 9/1993 |
| WO | WO-9940841 A1 | 8/1999 |

OTHER PUBLICATIONS

English Abstract for DE4210102A1.
International Search Report for PCT/US 2008/087158, dated Jun. 5, 2009.

* cited by examiner

*Primary Examiner* — Eric Winakur
*Assistant Examiner* — Chu Chuan (JJ) Liu (57) ABSTRACT

A sensor used to measure physiological characteristics of body tissues is provided. The physiological sensor includes a first light source assembly having a first light source in parallel with a second light source. Each of the first light source and the second light source have an anode and a cathode. A second light source assembly includes a third light source in parallel with a fourth light source. Each of the third light source and the fourth light source have an anode and a cathode. The anode of the first light source is electrically connected to the cathode of the second light source, the anode of said third light source, and the cathode of said fourth light source. The anode of the third light source is electrically connected to the cathode of the fourth light source.

19 Claims, 8 Drawing Sheets

PHYSIOLOGICAL SENSOR

BACKGROUND

Physiological sensor systems, such as pulse, tissue and cerebral oximeters, are used to measure a variety of physiological characteristics in body tissues using two wavelengths of light. The system generally includes a monitoring system connected to a sensor pad that adheres to the portion of the body being tested. The sensor pad includes a plurality of light sources in optical communication with at least one light detector. The light sources are activated by applying an excitation current source to an electrical wire connected to each light source. When activated, the light sources transmit light at specific wavelengths through the body tissue to the optical detector. The amount of light received by the light detector after attenuation by the body tissue is indicative of the physiological characteristic being tested.

To improve the accuracy of the measurement, or to enable the measurement of additional physiological characteristics, additional wavelengths of light can be used. This generally necessitates the addition of light sources requiring additional wires to carry the excitation potentials. Unfortunately, the addition of wires adds to the cost and complexity of the system. Moreover, monitoring systems are generally configured to work with sensor pads having a fixed number of wires. For example, if a monitoring system is configured to work with sensor pads having a three wire configuration, a sensor pad using additional light sources and having any more than three wires may not be compatible with the existing monitoring system.

One known method used to minimize the number of wires in a sensor pad when increasing the number of light sources includes having multiple light sources connected in a matrix of rows and columns of wires. The light sources in this configuration are activated by sequentially addressing the row and column of each light source with an excitation path. In this way, four wires provide connection and activation of four light sources. If pairs of light sources are connected in parallel, the same configuration of four wires can be used to connect and activate up to eight light sources. This configuration, however, requires a minimum of four wires and is limited to a maximum of eight light sources.

Accordingly, the embodiments described hereinafter were developed in light of these and other drawbacks associated with increasing the number of light sources in a physiological sensor without increasing the number of wires.

DETAILED DESCRIPTION

A physiological sensor that allows for an increased number of light sources without an increase in the number of wires is provided. Specifically, the physiological sensor can use four or six light sources in a three-wire configuration, or alternatively, up to twelve light sources in a four-wire configuration. In either embodiment, the physiological sensor includes one or more light source assemblies electrically connected to a monitoring system and in optical communication with at least one light detector. Each light source assembly includes at least one light source.

The arrangement of the light sources allows the physiological sensor to measure physiological characteristics of body tissue such as oxygen saturation or other various hemoglobin species with increased accuracy and without a significant increase in size or cost. The arrangement of the light sources may also measure concentrations of additional chromospheres in tissue besides hemoglobin. The spatial relationship of the light sources relative to the light detector may enhance spatial resolution and provide values at different depths, which may help in organ oxygen delivery monitoring.

Moreover, because the physiological sensor maintains a three or four wire configuration, the physiological sensor may be used with pre-existing monitoring systems, thus making the physiological sensor described herein backwards compatible. It is to be understood that the physiological sensor may be configured to work with any number of wires since the number of light assemblies (each having two light sources) is related to the number of wires. Specifically, the number of light source assemblies can be calculated by the equation: $N_{LSA}=N_W*(N_W-1)/2$, wherein $N_{LSA}$ is the number of light source assemblies and $N_W$ is the number of wires.

Figure 1:
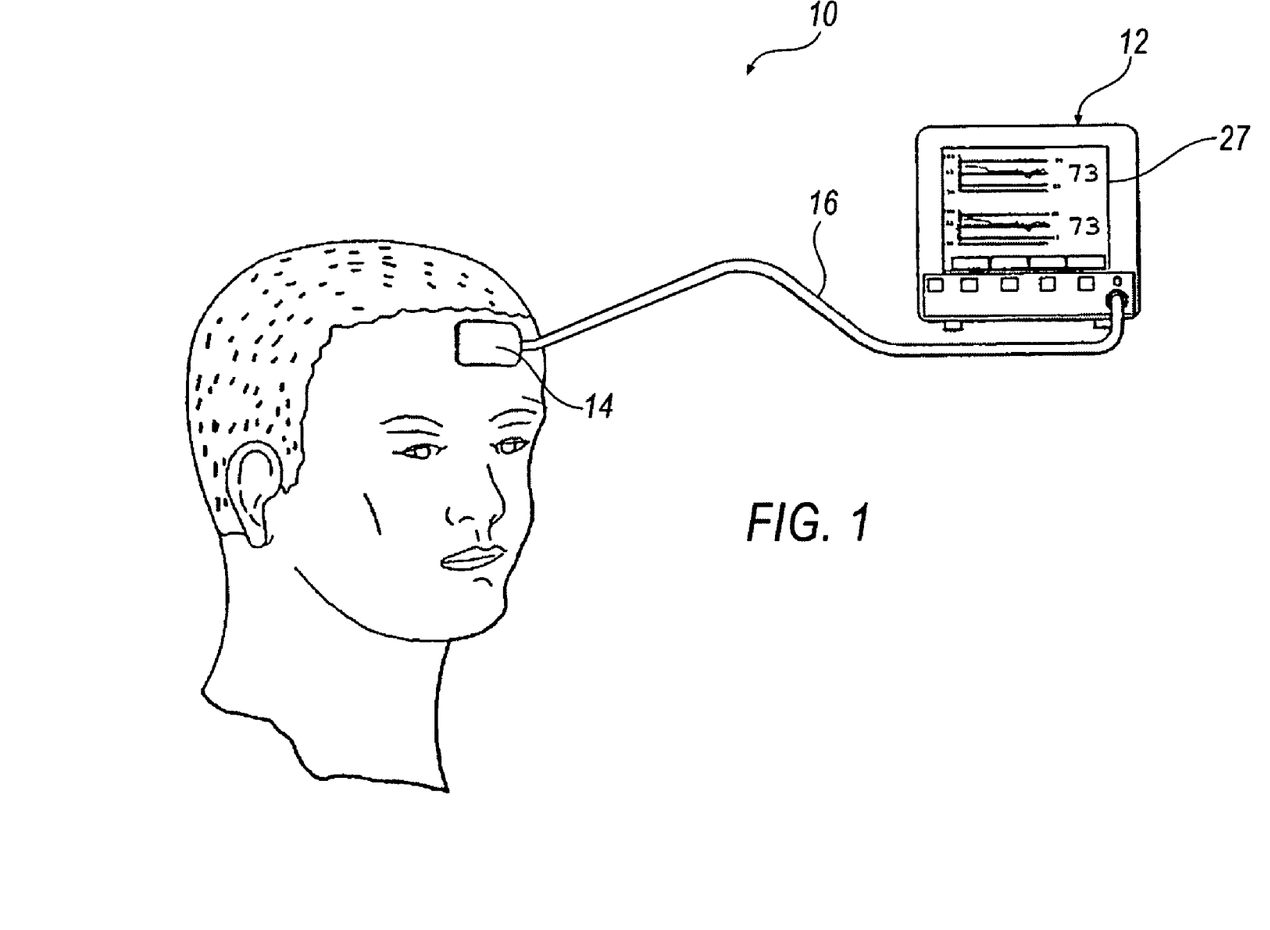
FIG. 1 is a perspective view of an exemplary physiological sensor according to an embodiment.
Figure 2:
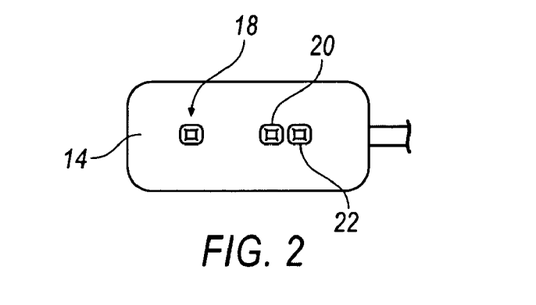
FIG. 2 is a bottom view of a pad of the physiological sensor, according to an embodiment.

FIG. 1 illustrates an exemplary physiological sensor system 10 that includes a monitoring system 12 connected to a sensor pad 14 through a cable 16. As best shown in FIG. 2, the sensor pad 14 includes a plurality of light sources 18 in optical communication with first and second light detectors 20, 22. It is to be appreciated that multiple light sources 18 may be disposed in multiple openings of the sensor pad 14. The plurality of light sources 18 may include any light source known in the art, including but not limited to, light emitting diodes, laser diodes or any combination thereof. Typically, the frequency of the light excitation and wavelength of the light source is dependent upon the application. For instance, in cerebral oximetry, pulse oximetry, or tissue oximetry applications, the light sources 18 may have a wavelength in the visible and/or infrared spectrum. For instance, the light sources 18 may have a wavelength between 600 nm and 1000 nm, including, but not limited to, a wavelength of 660 nm, 724 nm, 750 nm, 770 nm, 812 nm, 850 nm, 905 nm, or any combination thereof. It is to be understood that the light sources 18 may have other wavelengths to measure other physiological characteristics.

Figure 3:
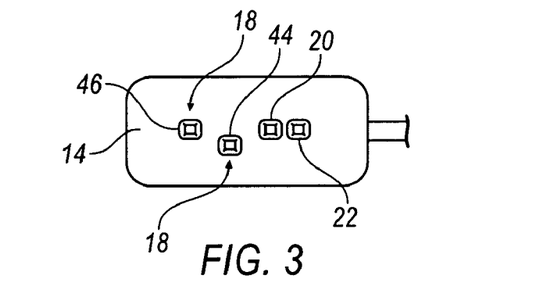
FIG. 3 is a bottom view of the physiological sensor according to another embodiment with multiple light source locations.
Figure 4:
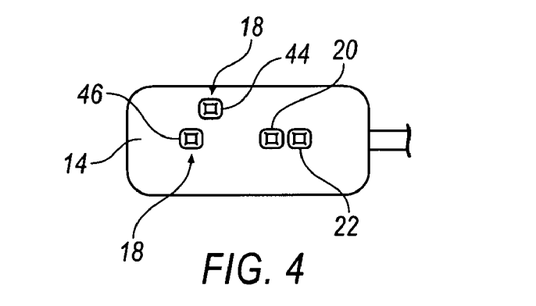
FIG. 4 is a bottom view of the physiological sensor according to third embodiment with multiple light source locations.

As shown in FIGS. 3 and 4, the plurality of light sources 18 may be mounted in two or more different physical locations on the sensor pad 14 or in openings in the pad 14. By adding additional light source assemblies when the physiological sensor system 10 is used as a cerebral oximeter sensor, the monitoring system 12 can obtain additional absorption spectra at additional wavelengths. The additional absorption spectra can help to better define the extinction curves for various blood and tissue chromophores, allowing more accurate determination of their relative concentrations. In one embodiment, each light source 18 is illuminated sequentially and independently, allowing measurement of light absorption at specific wavelengths by one or more of the light detectors 20, 22. Alternatively, two or more light sources 18 may be illuminated simultaneously to provide additional light output and an improved signal-to-noise ratio at specific wavelengths. This may be necessary because certain wavelengths of light do not penetrate as deeply into tissue as other wavelengths do. As will be discussed in greater detail below, illuminating several light sources 18 simultaneously may include multiple current sources. Alternatively, certain light sources may not have the same light output as others. Simultaneously illuminating two or more of these lower output light sources can increase the effective light output, improving signal-to-noise ratio and stability.

In another embodiment, the physiological sensor system 10 may be used for fractional oximetry to measure fractional oxygen saturation and additional hemoglobin species in deep tissue of the brain, other organs, skin, or in skeletal muscle tissue. By selecting wavelengths of light appropriately, additional fractional concentrations of other hemoglobin species such as carboxyhemoglobin and methemoglobin can be determined. Most noninvasive oximeters measure functional hemoglobin oxygen saturation, which is defined as the ratio of oxyhemoglobin to the unbound hemoglobin that is available for oxygen binding. As such, it does not measure or take into effect the proportion of hemoglobin that is bound to other compounds such as carbon monoxide (carboxyhemoglobin) or hydrogen sulfide (sulfhemoglobin). Additional species of hemoglobin such as methemoglobin, where the ferrous iron has been oxidized to ferric iron, are not measured either. By incorporating additional wavelengths of light, the effect of additional chromophores with unique extinction curves can be measured, enabling estimation of the fraction of each hemoglobin compound, or fractional saturation.

In yet another embodiment, some of the plurality of light sources 18 may be used for cerebral or tissue oximetry and others of the plurality of light sources 18 may be used for pulse oximetry to measure arterial blood hemoglobin oxygen saturation. This allows the physiological sensor system 10 to measure various physiological characteristics with the same sensor pad 14. In this embodiment, a first light source assembly 44 may use selected wavelengths of light and be located a sufficient distance from one of the detectors 20, 22 to measure cerebral oxygen saturation while a second light source assembly 46 may use wavelengths suited for measurement of arterial oxygen saturation using reflectance pulse oximetry and would therefore be located close to another of the light detectors 20, 22. Alternatively, the first light detector 20 may be used to measure arterial oxygen saturation based on the spatial relationship of the plurality of light sources 18. This embodiment also allows arterial saturation of deeper tissues to be measured because the depth of penetration of photons is proportional to the separation distance between the light source 18 and the light detector 20, 22.

In yet another embodiment, the plurality of light sources 18 can be spatially arranged to increase the accuracy of the measurements. For instance, the first light source assembly 44 can have different wavelengths that penetrate less deeply into the body tissue than other light source assemblies. For instance, as shown in FIG. 3, placing the first light source assembly 44 closer to the light detector 20 and slightly offset from the first light source assembly 46 allows the first light source assembly 44 to penetrate into the body tissue shallower than the second light source assembly 46. Likewise, placing the second light source 46 further away from the light detector 20 and slightly offset from the first light source assembly 44 causes light generated by the second light source assembly 46 to penetrate deeper into the body tissue. Alternatively, as shown in FIG. 4, the first light source assembly 44 may be spaced away from the second light source assembly 46 and more offset from the second light source assembly 46 to achieve a similar result. In this embodiment, the ratios of the signals from each of the light detectors 20, 22 can be computed using both light source assemblies 44, 46.

In yet another embodiment, the physiological sensor system 10 may contain a plurality of sensor pads 14 and each sensor pad 14 may contain at least one light source assembly 44 and one light detector 20. This arrangement of the physiological sensor system 10 may be used to measure two physiological parameters including, but not limited to, cerebral blood saturation and arterial blood saturation. The cerebral measurement may require a low skin perfusion site on the forehead to reduce interference from extra-cranial signals. However, arterial blood oxygen saturation may require high skin perfusion. Thus, in one embodiment, for cerebral oximetry, the sensor pad 14 may be placed on the forehead directly below the hair line. On the other hand, for pulse oximetry, the sensor pad 14 may be placed on the forehead directly above the eyes. In this embodiment, a single sensor pad 14 may be inconvenient to use at least for an adult patient. Therefore, two sensor pads 14 may be used.

Figure 5:
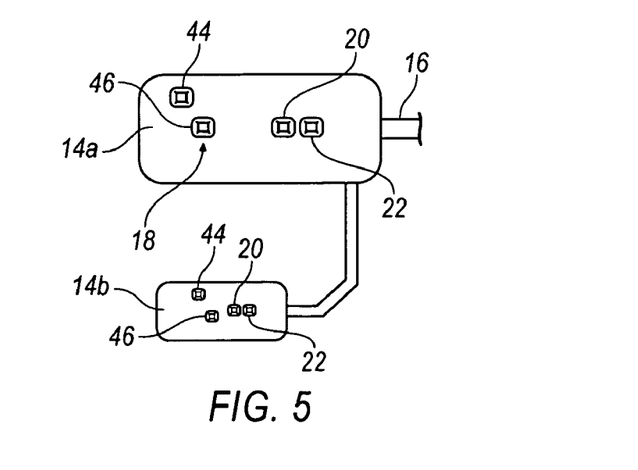
FIG. 5 is a bottom view of a physiological sensor having a plurality of sensing pads.

Referring now to FIG. 5, in one exemplary approach, the physiological sensor system 10 includes a first sensor pad 14A and a second sensor pad 14B. The first sensor pad 14A may be used, for instance, for tissue oximetry, and the second sensor pad 14B may be used, for instance, for pulse oximetry. The first sensor pad 14A may include the light source assemblies 44, 46, in optical communication with the first and second light detectors 20, 22. It is to be appreciated that the first sensor pad 14A may include any number of light source assemblies 44, 46 and any number of light detectors 20, 22. Likewise, the second sensor pad 14B may include the light source assemblies 44, 46, in optical communication with the first and second light detectors 20, 22. It is to be appreciated that the second sensor pad 1413 may include any number of light source assemblies 44, 46 and any number of light detectors 20, 22.

Other cases where two or more sensor pads 14 may be used include measuring cerebral oxygenation from at least two sites of the brain, or measuring cerebral and tissue oxygenation simultaneously in infants. In this embodiment, the physiological sensor system 10 may include at least two sensor pads 14, each having at least two light detectors 20, 22 and at least two light source assemblies 42, 46. The light source assemblies 42, 46 may be connected as described above and excited sequentially in time.

Figure 6:
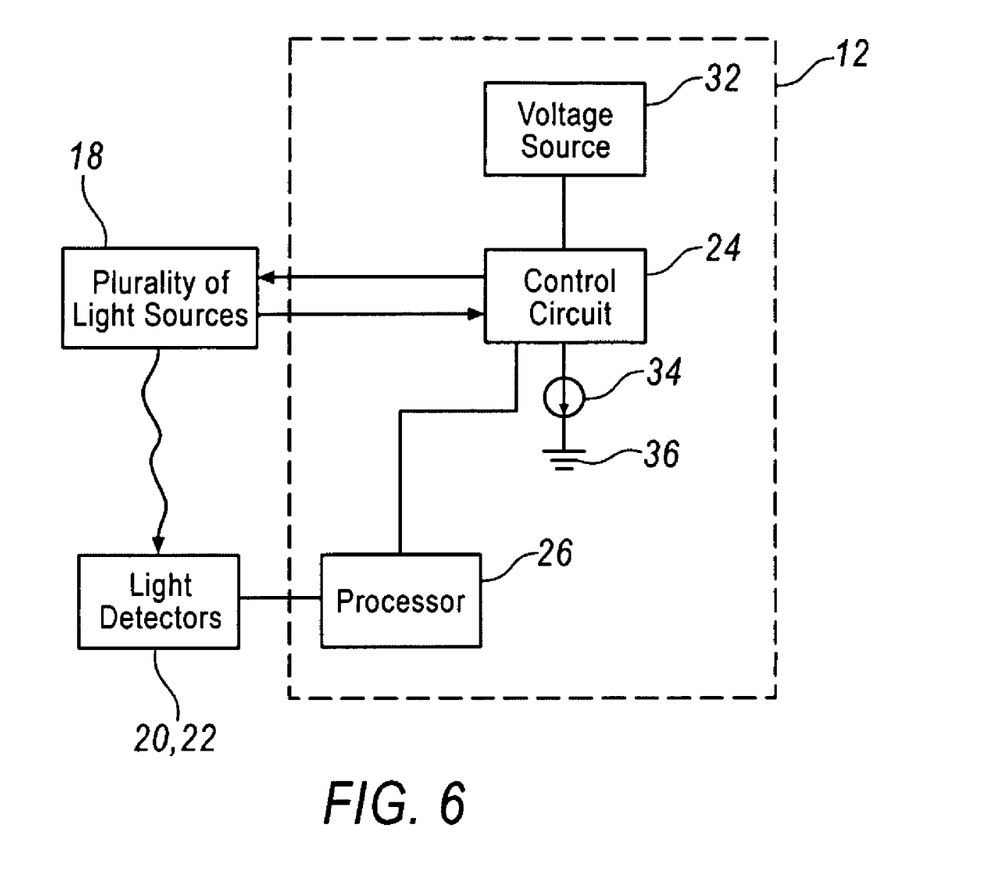
FIG. 6 is a block diagram illustrating an exemplary control scheme, according to an embodiment.

As shown in FIG. 6, monitoring system 12 includes a control circuit 24 and a processor 26 in communication with the plurality of light sources 18 and light detectors 20, 22. The processor 26 is configured to receive signals from light detectors 20, 22 and converts the signals into data that indicates the physiological characteristics of the body tissue. Furthermore, the processor 26 controls the control circuit 24 as will be discussed in greater detail below. It is to be understood that the control circuit 24 may alternatively be controlled by a dedicated processor (not shown) other than the processor 26 shown in FIG. 6. The monitoring system 12 may output the data to a display 27 as shown in FIG. 1.

Figure 7:
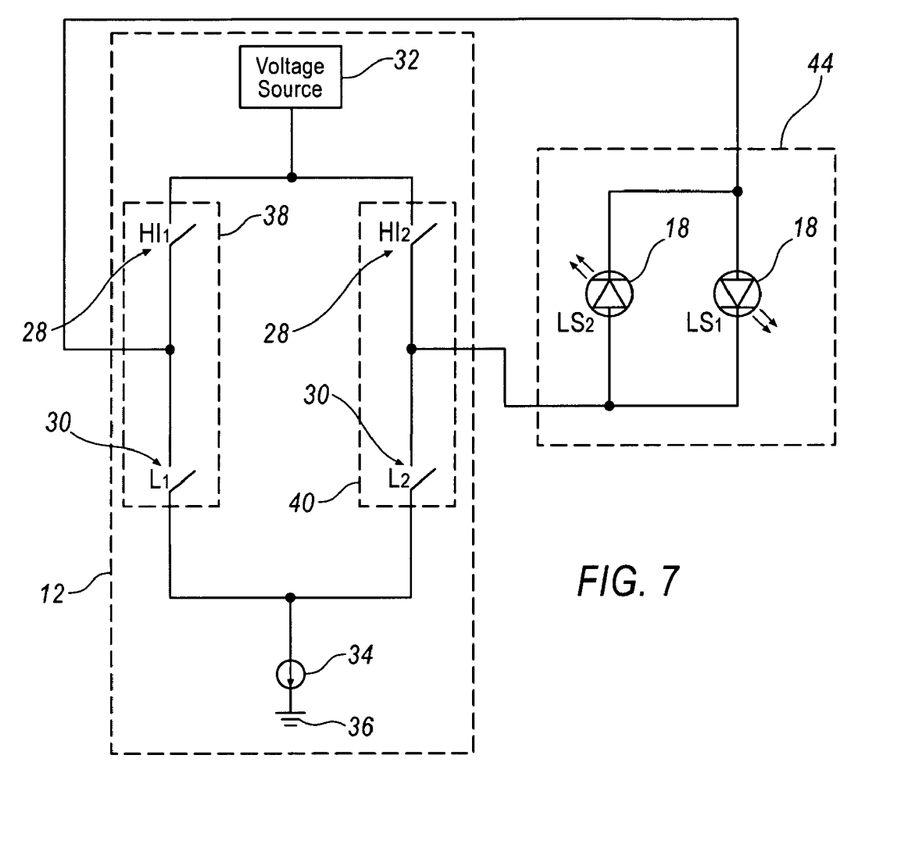
FIG. 7 is a diagram illustrating an exemplary control circuit and light assembly, according to an embodiment.

FIG. 7 illustrates an exemplary control circuit 24, which includes at least one high switch 28 and at least one low switch 30. As discussed in greater detail below, it is to be understood that the high switch 28 connects the light sources 18 to a higher potential than the low switch 30. The high switch 28 and the low switch 30 may be any switch known in the art, and even the same type of switch. For instance, the high switch 28 and the low switch 30 may be transistors. In one embodiment, the high switch 28 may be a PMOS type transistor and the low switch 30 may be an NMOS type transistor. The high switch 28 and the low switch 30 may be connected in an H-Bridge configuration.

The at least one high switch 28 and the at least one low switch 30 are controlled by the processor 26 in the monitoring system 12. In other words, the processor 26 opens and closes the at least one high switch 28 and the at least one low switch 30 of the control circuit 24 to activate a select combination of the plurality of light sources 18. The monitoring system 12 includes a voltage source 32 electrically connected to the control circuit 24 for providing voltage to the control circuit 24 and the plurality of light sources 18. In addition, the monitoring system 12 may further include a current source 34 that causes current to flow from the voltage source 32 to ground 36. The low switches 30 connect each of the plurality of light sources 18 to the current source 34. The current source 34 is connected to the ground 36 at a ground potential. It is to be understood that the low switches 30 may connect to the plurality of light sources 18 directly to the ground potential. Otherwise, in at least one embodiment, there is no structural or functional difference between the high switches 28 and the low switches 30.

Figure 8:
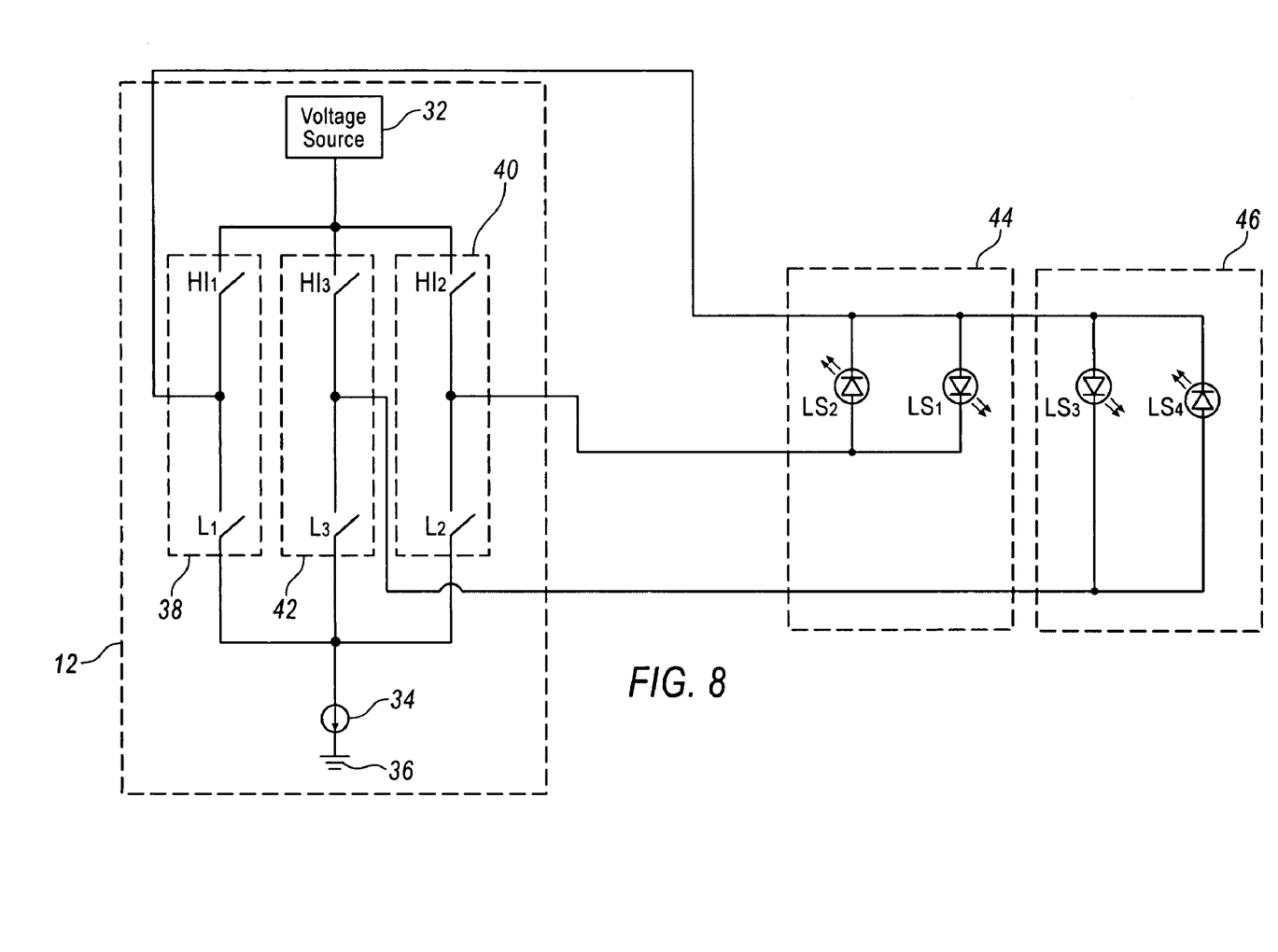
FIG. 8 is a diagram illustrating another exemplary control circuit and light assembly, according to an embodiment.

The control circuit 24 may include any number of high switches 28 or low switches 30. For instance, as shown in FIG. 7, the control circuit 24 includes a first high switch HI1 in series with a first low switch L1, the combination of which defines a first switch pair 38. Likewise, the control circuit 24 includes a second high switch HI2 in series with a second low switch L2, the combination of which defines a second switch pair 40. It is to be understood that the control circuit 24 may include any number of high switches 28 and low switches 30 to define any number of switch pairs. For instance, referring to FIG. 8, the control circuit 24 may include a third high switch HI3 and a third low switch L3 in series with the third high switch HI3 to define a third switch pair 42. As shown in FIG. 8, the first switch pair 38 is in parallel with the second switch pair 40 and the third switch pair 42.

Each high switch 28 and each low switch 30 have an anode and a cathode. The anode of the high switch 28 directly or indirectly connects to the voltage source 32 and the cathode of the low switch 30 directly or indirectly connects to a lower potential (i.e., a ground potential 36 or the current source 34). When the control circuit 24 includes multiple high switches 28, the anodes of each of the high switches 28 are electrically connected to one another. For example, referring to FIG. 7, the anode of the first high switch HI1 may be electrically connected to the anode of the second high switch HI2. Similarly, when the control circuit 24 includes multiple low switches 30, the cathodes of each of the low switches 30 may be electrically connected. Again referring to FIG. 7, the cathode of the first low switch L1 is electrically connected to the cathode of the second low switch L2.

In operation, the processor 26 closes one of the high switches 28 and one of the low switches 30 to activate one of the plurality of light sources 18. In one embodiment, each light source is connected to two switch pairs. The light source is powered by the voltage source 32 when the high switch 28 in one of the switch pairs is closed and the low switch 30 in another switch pair is closed, completing an electrical circuit. It is to be understood that multiple light sources may be illuminated by closing more than one high switch 28 and/or more than one low switch 30. However, closing the high switch 28 and the low switch 30 in the same switch pair will cause an electrical short, and the light source will not illuminate. In other words, the light source does not operate when the high switch 28 and the low switch 30 from the same switch pair are both closed. To prevent an electrical short, the processor 26 opens the low switch 30 in the switch pair when the high switch 28 in the switch pair is closed. Therefore, the light source is electrically connected to the high switch 28 in one switch pair and the low switch 30 in another switch pair. It is to be understood that both the high switch 28 and the low switch 30 may be open at the same time.

As shown in FIG. 7, the physiological sensor 10 includes a first light source assembly 44 that is defined by at least one of the plurality of light sources 18 and electrically connected to the control circuit 24. As shown, the first light source assembly 44 includes a first light source LS1 in parallel with a second light source LS2. As previously discussed, the first light source LS1 and the second light source LS2 may be light emitting diodes or laser diodes. Each of the first light source LS1 and the second light source LS2 have an anode and a cathode. The anode of the first light source LS1 is electrically connected to the cathode of the second light source LS2. In addition, the cathode of the first light source LS1 is electrically connected to the anode of the second light source LS2. Therefore, although disposed in parallel with the second light source LS2, the first light source LS1 has an opposite polarity to the second light source LS2. The first light source LS1 and the second light source LS2 are each electrically connected to at least two switch pairs. Specifically, the first light source LS1 is electrically connected to the first high switch HI1 and the second low switch L2, and the second light source LS2 is electrically connected to the second high switch HI2 and the first low switch L1. The first high switch HI1 is in series with the second low switch L2 when the first high switch HI1 and the second low switch L2 are closed. Likewise, the second high switch HI2 is in series with the first low switch L1 when the second high switch HI2 and the first low switch L1 are closed. In this embodiment, only one of the plurality of light sources 28 may be illuminated at any time since only one of the first high switch HI1 and the second high switch HI2 may be closed because closing both the first high switch HI1 and the first low switch L1 or the second high switch HI2 and the second low switch L2 would cause an electrical short. Therefore, the processor 26 opens the first low switch L1 when the first high switch HI1 is closed. Likewise, the processor 26 opens the second low switch L2 when the second high switch HI2 is closed.

It is to be understood that the physiological sensor system 10 may include any number of light source assemblies. For instance, referring to FIG. 8, the system 10 further includes a second light source assembly 46 defined by at least one of the plurality of light sources 18 and electrically connected to the monitoring system 12. The second light source assembly 46 includes a third light source LS3 in parallel with a fourth light source LS4. Although disposed in parallel with the fourth light source LS4, the third light source LS3 has an opposite polarity than the fourth light source LS4. Each of the third light source LS3 and the fourth light source LS4 have an anode and a cathode. The anode of the third light source LS3 is electrically connected to the cathode of the fourth light source LS4. The cathode of the third light source LS3 is electrically connected to the anode of the fourth light source LS4. In one embodiment, as shown in FIG. 8, the anode of the third light source LS3 is also electrically connected to the anode of the first light source LS1 and the cathode of the second light source LS2. As in the previous embodiment, the first light source LS1 is electrically connected to the first high switch HI1 and the second low switch L2 and the second light source LS2 is electrically connected to the second high switch HI2 and the first low switch L1. In this embodiment, the third light source LS3 is electrically connected to the first high switch HI1 and the third low switch L3. The fourth light source LS4 is electrically connected to the third high switch HI3 and the first high switch HI1. Again, the third high switch HI3 is in series with the third low switch L3 to make up the third switch pair 42.

In this embodiment, it is possible for the processor 26 to illuminate more than one of the plurality of light sources 18 simultaneously. For instance, the processor 26 may close the first high switch HI1 and the second low switch L2 to illuminate the first light source LS1. The processor 26 may then close the third low switch L3 to illuminate the third light source LS3 since both the first light source LS1 and the third light source LS3 receive power from the voltage source 32 when the first high switch HI1 is closed. It is to be appreciated that the processor 26 may close the third low switch L3 at the same time as closing the second low switch L2 to illuminate the third light source LS3 simultaneously with the first light source LS1, or the processor 26 may close the third low switch L3 after closing the second low switch L2 to illuminate the third light source LS3 sequentially with the first light source LS1. Alternatively, the processor 26 may close the second high switch HI2 and the first low switch L1 to illuminate the second light source LS2, and by closing the third high switch HI3 while the second high switch HI2 and the first low switch L1 are closed, the processor 26 additionally illuminates the fourth light source LS4. Therefore, in this embodiment, the processor 26 may illuminate two of the plurality of light sources 18.

Figure 9:
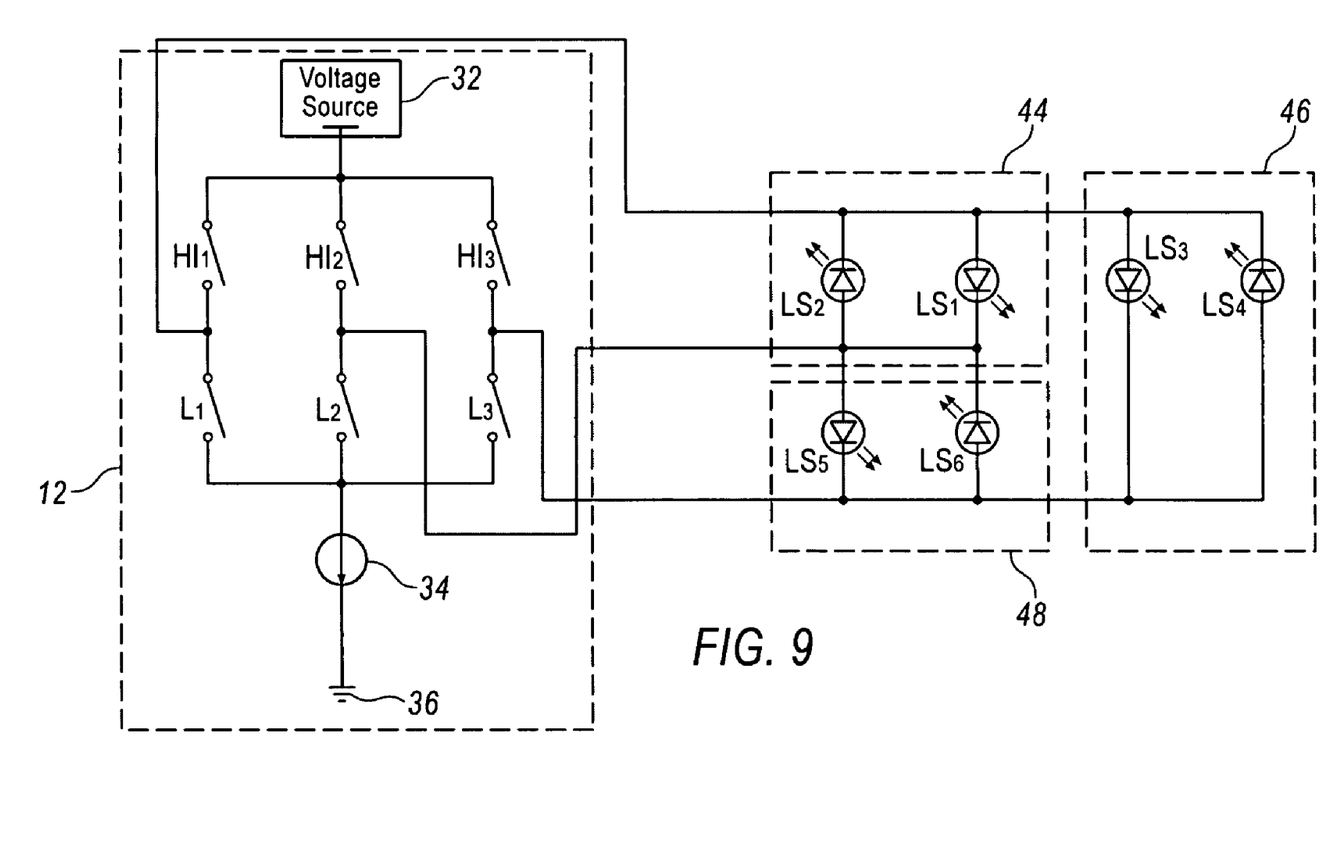
FIG. 9 is a diagram illustrating another exemplary control circuit and light assembly, according to an embodiment.

Referring now to FIG. 9, the physiological sensor system 10 further includes a third light source assembly 48 that includes a fifth light source LS5 in parallel with a sixth light source LS6. Although disposed in parallel with the sixth light source LS6, the fifth light source LS5 has an opposite polarity than the sixth light source LS6. Each of the fifth light source LS5 and the sixth light source LS6 have an anode and a cathode. The anode of the fifth light source LS5 is electrically connected to the cathode of the first light source LS1, the anode of the second light source LS2, and the cathode of the sixth light source LS6. The cathode of the fifth light source LS5 is electrically connected to the cathode of the third light source LS3, the anode of the fourth light source LS4, and the anode of the sixth light source LS6. The anode of the sixth light source LS6 is electrically connected to the cathode of the third light source LS3 and the anode of the fourth light source LS4. The cathode of the sixth light source LS6 is electrically connected to the cathode of the first light source LS1 and the anode of the second light source LS2. As in the previous embodiment, the processor 26 may illuminate more than one of the plurality of light sources 18 simultaneously. For instance, the processor 26 may close the first high switch HI1 and the second low switch L2 to illuminate the first light source LS1. At the same time, the processor 26 may close the third low switch L3 to illuminate the third light source LS3. Therefore, the processor 26 may illuminate more than one of the plurality of light sources 18 simultaneously.

Figure 10:
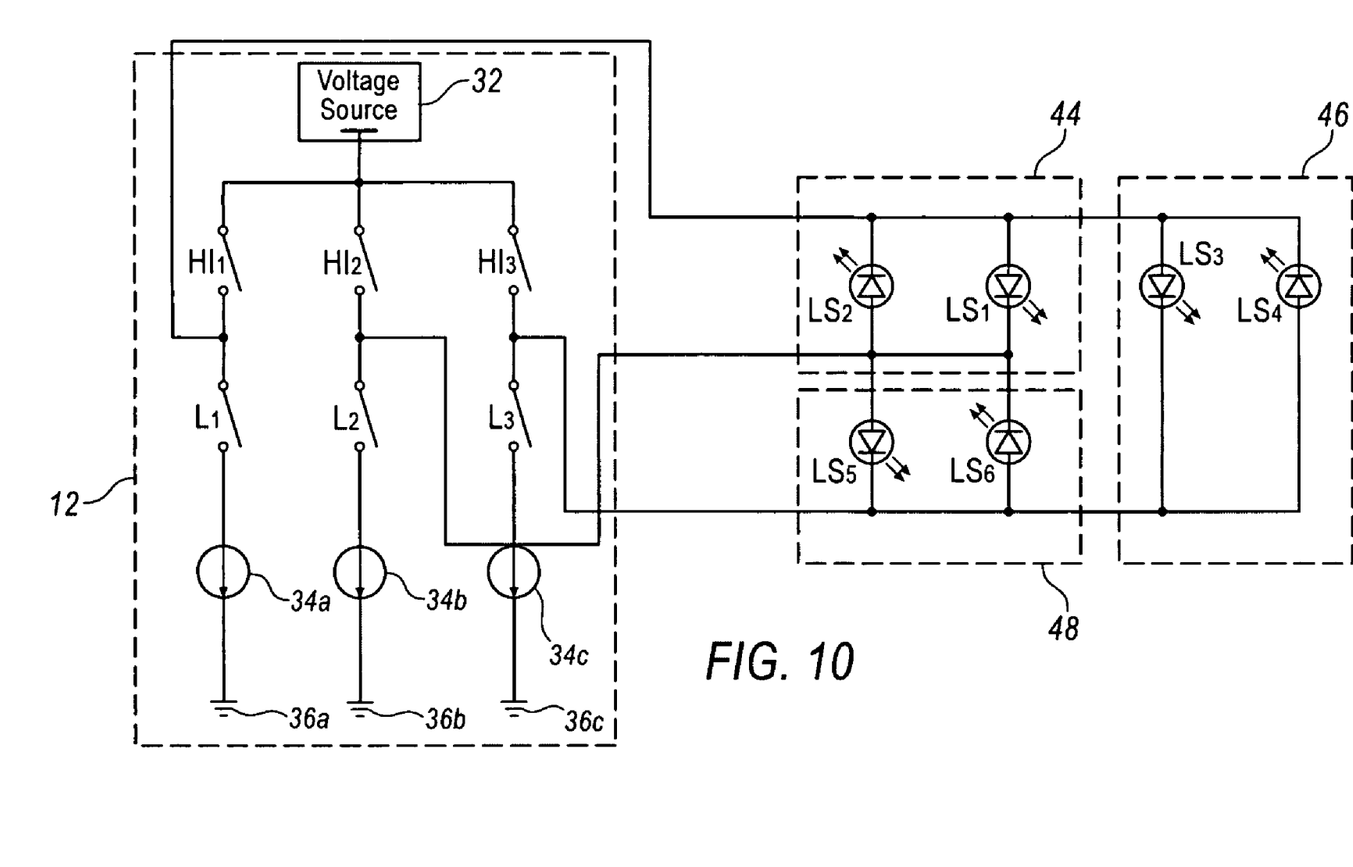
FIG. 10 is a diagram illustrating the exemplary control circuit and light assembly as set forth in FIG. 9 having multiple current sources.

In one exemplary embodiment, to illuminate more than one of the plurality of light sources 18 simultaneously, the physiological sensor system 10 may include more than one current sources 34. Referring now to FIG. 10, the physiological sensor 10 includes a first current source 34A electrically connected to the first low switch L1, a second current source 34B electrically connected to the second low switch L2, and a third current source 34C electrically connected to the third low switch L3. The current sources 34A, 34B, and 34C help to ensure that the light sources 18 maintain a minimum amount of brightness when the light sources 18 are simultaneously illuminated.

Figure 11:
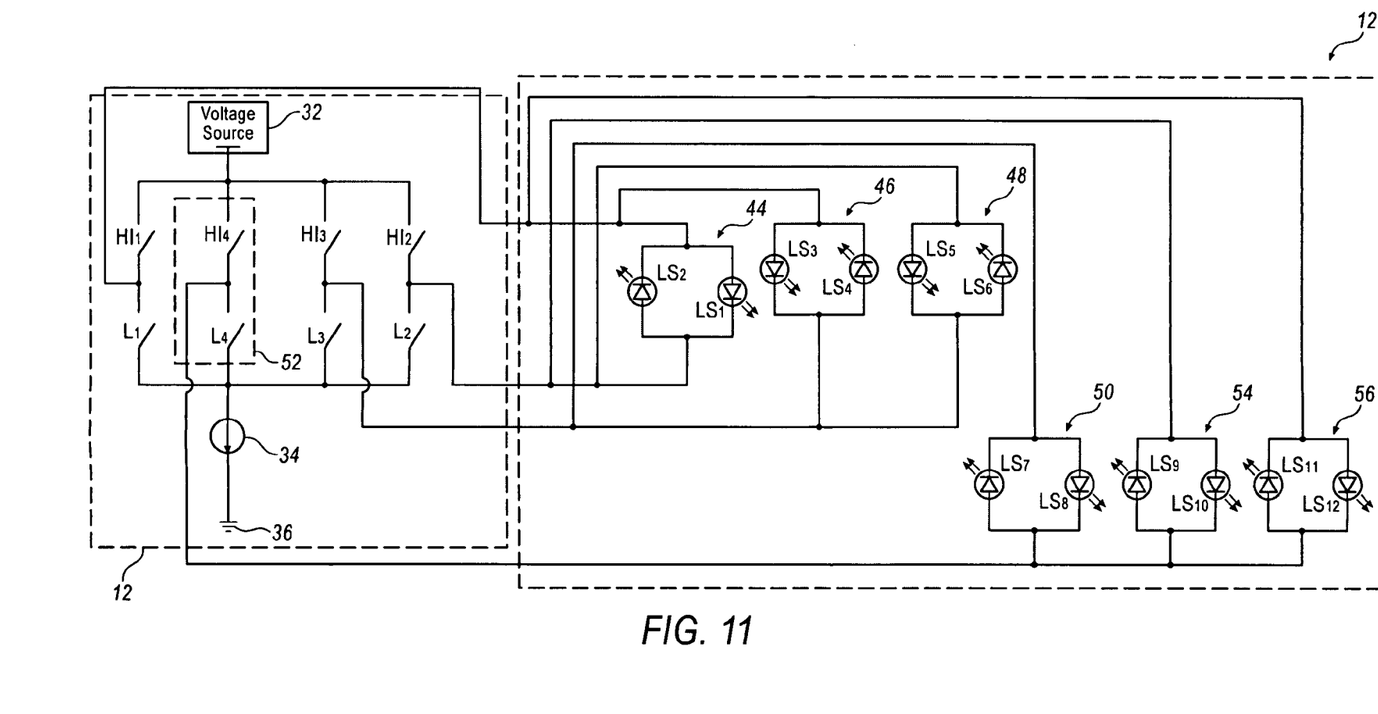
FIG. 11 is a diagram illustrating another exemplary control circuit and light assembly, according to an embodiment.

Again, it is to be understood that the physiological sensor system 10 may include any number of light source assemblies. For instance, referring to FIG. 11, the physiological sensor system 10 further includes a fourth light source assembly 50, a fifth light source assembly 54, and a sixth light source assembly 56. In addition, the control circuit 24 includes a fourth switch pair 52 having a fourth high switch HI4 in series with a fourth low switch L4. The fourth light source assembly 50 includes a seventh light source LS7 in parallel with an eighth light source LS8. The seventh light source LS7 and the eighth light source LS8 each have an anode and a cathode. The anode of the seventh light source LS7 is electrically connected to the fourth high switch HI4 and the cathode of the seventh light source LS7 is electrically connected to the third ground 36 source. The anode of the eighth light source LS8 is electrically connected to the third high switch HI3 and the cathode of the eighth light source LS8 is electrically connected to the fourth low switch L4. The fifth light source assembly 54 includes a ninth light source LS9 in parallel with a tenth light source LS10. The ninth light source LS9 and the tenth light source LS10 each have an anode and a cathode. The anode of the ninth light source LS9 is electrically connected to the fourth high switch HI4 and the cathode of the ninth light source LS9 is electrically connected to the second low switch L2. The anode of the tenth light source LS10 is electrically connected to the second high switch HI2 and the cathode of the tenth light source LS10 is electrically connected to the fourth low switch L4. The sixth light source assembly 56 includes an eleventh light source LS11 in parallel with a twelfth light source LS12. The eleventh light source LS11 and the twelfth light source LS12 each have an anode and a cathode. The anode of the eleventh light source LS11 is electrically connected to the fourth high switch HI4 and the cathode of the eleventh light source LS11 electrically connected to the first low switch L1. The anode of the twelfth light source LS12 is electrically connected to the first high switch HI1 and the cathode of the twelfth light source LS12 is electrically connected to the fourth low switch L4. As in the previous embodiments, the processor 26 may illuminate one or more of the plurality of light sources 18. For instance, the processor 26 may close the first high switch HI1, the second low switch L2, and the fourth low switch L4 to illuminate the first light source LS1, the third light source LS3, and the twelfth light source LS12. Alternatively, the processor 26 may close the first high switch HI1, the third high switch HI3, the fourth high switch HI4, and the second low switch L2 to illuminate the first light source LS1, the sixth light source LS6, and the ninth light source LS9.

It is to be understood that the physiological sensor system 10 may include any number of light source assemblies, each including any number of light sources 18. Also, the processor 26 may close different combinations of the high switches 28 and the low switches 30 to illuminate alternative combinations of the plurality of light sources 18.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A physiological sensor comprising:
   at least one sensor pad;
   at least one light source assembly disposed on said at least one sensor pad and having a plurality of light sources each arranged in anti-parallel pairs;
   a plurality of switches in communication with the light source assembly via a plurality of wires, wherein actuating a select combination of the plurality of switches activates at least one of the plurality of light sources and wherein a number of light sources disposed on the sensor pad is greater than a number of wires connecting the plurality of switches to the at least one light source assembly; and
   wherein said at least one light source assembly is configured to measure at least one physiological characteristics of body tissue.

2. The sensor of claim 1, wherein said physiological characteristics of body tissue include at least one of cerebral oxygenation, fractional oximetry, pulse oximetry, tissue oxygenation, and concentrations of various tissue chromophores.

3. The sensor of claim 1, wherein each of said light sources have a wavelength in at least one of a visible and infrared spectrum.

4. The sensor of claim 1, wherein said at least one light source assembly is further defined as a plurality of light source assemblies and said plurality of light source assemblies are illuminated sequentially.

5. The sensor of claim 1, further comprising at least one light detector disposed on said sensor pad and spaced from said at least one light source assembly.

6. The sensor of claim 5, wherein said at least one light source assembly is further defined as a plurality of light source assemblies, and wherein at least one of said plurality of light source assemblies is closer to said at least one light detector than another of said plurality of light source assemblies.

7. The sensor of claim 6, wherein one of said plurality of light source assemblies is offset from said first light detector relative to another of said plurality of light source assemblies.

8. The sensor of claim 7, wherein light generated by one of said plurality of light source assemblies penetrates body tissue shallower than light generated by another of said plurality of light source assemblies.

9. The sensor of claim 1, further comprising a current source electrically connected to one of said light source assemblies.

10. The sensor of claim 1, further comprising a plurality of current sources, wherein each of said plurality of current sources is electrically connected to at least one of said light source assemblies.

11. The sensor of claim 1, further comprising a plurality of wires electrically connected to said plurality of light source assemblies.

12. The sensor of claim 1, wherein said sensor pad defines at least one opening and at least one of said plurality of light sources is disposed in said at least one opening.

13. The sensor of claim 12, wherein said at least one sensor pad is further defined as a plurality of sensor pads and said at least one light source assembly is further defined as a plurality of light source assemblies, and wherein at least one of said plurality of light source assemblies is disposed in said at least one opening of said at least one of said plurality of sensor pads.

14. A physiological sensor system comprising:
    a sensor having at least one sensor pad and a plurality of light sources disposed on the sensor pad, wherein each light source is arranged in an anti-parallel pair with at least one other light source;
    wherein the sensor is electrically connected configured to receive signals from a monitoring device having a plurality of switches and wherein a number of wires connecting the sensor to the monitoring device is less than a number of light sources disposed on the sensor,
    wherein the signals received from select combinations of the plurality of switches activate select combinations of the plurality of light sources.

15. The physiological sensor system of claim 14, wherein enabling select combinations of the plurality of switches activate one of the light sources in the anti-parallel pair.

16. The physiological sensor system of claim 14, wherein enabling select combinations of the plurality of switches in a predetermined sequence activates each of the plurality of light sources according to a predetermined sequence.

17. The physiological sensor system of claim 14, wherein the plurality of switches are arranged in pairs and no more than one switch in each pair is enabled at any time.

18. The physiological sensor system of claim 14, wherein a maximum number of light source assemblies disposed on the sensor is defined by the following equation: $N_{LSA} = N_W * (N_W - 1)/2$, wherein $N_{LSA}$ is the number of light source assemblies and $N_W$ is the number of wires connecting the sensor to the monitoring device.

19. A physiological sensor comprising:
    a first light source assembly and a second light source assembly, each having two light sources arranged in an anti-parallel pair and electrically connected to a first pair of switches, a second pair of switches, and a third pair of switches via a plurality of wires, wherein no more than three wires connect the first and second light source assemblies to the first and second pairs of switches,
    wherein one light source in the first light source assembly is configured to activate when one switch from both the first and second pairs of switches are enabled and wherein another light source from the first light source assembly is configured to activate when another switch from both the first and second pairs of switches are enabled.

* * * * *